United States Patent
Aranega Jimenez et al.

(10) Patent No.: US 10,537,591 B2
(45) Date of Patent: Jan. 21, 2020

(54) METHOD FOR PROMOTING MUSCLE REGENERATION

(71) Applicant: Universidad de Jaen, Jaen (ES)

(72) Inventors: Amelia Eva Aranega Jimenez, Jaen (ES); Diego Franco Jaime, Jaen (ES); Francisco Hernandez Torres, Jaen (ES); Estefania Lozano Velasco, Jaen (ES); Daniel Vallejo Pulido, Jaen (ES)

(73) Assignee: UNIVERSIDAD DE JAEN, Jaen (ES)

( * ) Notice: Subject to any disclaimer, the term of this patent is extended or adjusted under 35 U.S.C. 154(b) by 0 days.

(21) Appl. No.: 15/573,417

(22) PCT Filed: May 12, 2016

(86) PCT No.: PCT/ES2016/070362
§ 371 (c)(1),
(2) Date: Nov. 10, 2017

(87) PCT Pub. No.: WO2016/181011
PCT Pub. Date: Nov. 17, 2016

(65) Prior Publication Data
US 2019/0111071 A1 Apr. 18, 2019

(30) Foreign Application Priority Data

May 12, 2015 (ES) .................................. 201530645

(51) Int. Cl.
| | |
|---|---|
| *A61K 31/7105* | (2006.01) |
| *C12N 15/113* | (2010.01) |
| *A61P 21/00* | (2006.01) |
| *A61K 9/00* | (2006.01) |
| *C12N 5/077* | (2010.01) |
| *C12N 15/86* | (2006.01) |

(52) U.S. Cl.
CPC ........ *A61K 31/7105* (2013.01); *A61K 9/0019* (2013.01); *A61P 21/00* (2018.01); *C12N 5/0659* (2013.01); *C12N 15/113* (2013.01); *C12N 15/86* (2013.01); *C12N 2310/113* (2013.01); *C12N 2310/14* (2013.01); *C12N 2710/10041* (2013.01); *C12N 2740/10041* (2013.01); *C12N 2750/14141* (2013.01)

(58) Field of Classification Search
None
See application file for complete search history.

(56) References Cited

FOREIGN PATENT DOCUMENTS

| | | |
|---|---|---|
| ES | 2 559 106 A1 | 2/2016 |
| WO | 2016/181011 A1 | 11/2016 |

OTHER PUBLICATIONS

Lozano-Velasco et al. Molecular and Cellular Biology vol. 35(17):2892-2909, 2015.*
Buckingham et al., "Distinct and dynamic myogenic populations in the vertebrate embryo," *Current Opinion in Genetics & Development* 19:444-453, 2009.
Guddati et al., "Embryonic Stem Cells Overexpressing Pitx2c Engraft in Infarcted Myocardium and Improve Cardiac Function," *International Heart Journal* 50(6):783-799, 2009.
Hebert et al., "The Role of Pitx2 in Maintaining the Phenotype of Myogenic Precursor Cells in the Extraocular Muscles," *PLoS ONE* 8(3):e58405, 2013. (13 pages).
Koning et al., "A global downregulation of microRNAs occurs in human quiescent satellite cells during myogenesis," *Differentiation* 84:314-321, 2012.
Lozano-Velasco et al., "A Pitx2-MicroRNA Pathway Modulates Cell Proliferation in Myoblasts and Skeletal-Muscle Satellite Cells and Promotes Their Commitment to a Myogenic Cell Fate," *Molecular and Cellular Biology* 35(17):2892-2909, 2015.
Lozano-Velasco et al., "Pitx2c modulates Pax3+/Pax7+ cell populations and regulated Pax3 expression by repressing miR27 expression during myogenesis," *Developmental Biology* 357:165-178, 2011.
Martínez-Fernandez et al., "Pitx2c Overexpression Promotes Cell Proliferation and Arrests Differentiation in Myoblasts," *Developmental Dynamics* 235:2930-2939, 2006.
Wu et al., "MiR-20a and miR-106b negatively regulate autophagy induced by leucine deprivation via suppression of *ULK1* expression in C2C12 myoblasts," *Cellular Signalling* 24:2179-2186, 2012.
Zhang et al., "Silencing miR-106b improves palmitic acid-induces mitochondrial dysfunction and insulin resistance in skeletal myocytes," *Molecular Medicine Reports* 11:3834-3841, 2015.

* cited by examiner

*Primary Examiner* — Sean Mcgarry
(74) *Attorney, Agent, or Firm* — Seed IP Law Group LLP

(57) ABSTRACT

The invention solves the problem of providing new therapies that are effective in the treatment of muscular dystrophies through the use of compositions comprising a compound capable of reducing the expression of miRNA-106b in muscle satellite stem cells of a human or animal subject with respect to the expression observed in the absence of the compound in said cells.

17 Claims, 12 Drawing Sheets
Specification includes a Sequence Listing.

SEQUENCE LISTING

```
<160> NUMBER OF SEQ ID NOS: 3

<210> SEQ ID NO 1
<211> LENGTH: 2337
<212> TYPE: DNA
<213> ORGANISM: Homo sapiens
<220> FEATURE:
<221> NAME/KEY: misc_feature
<222> LOCATION: (1)...(2337)
<223> OTHER INFORMATION: Genbank No. NM_000325

<400> SEQUENCE: 1
gttaggccaa cagggaagcg cggagccgca gatctggtcc gtcgctcgcc tgggtgcctg      60
gagctgagct gcggcaaggc ccggctcctg ttcgaccgcc cgagggggtgt gcgtgtgcgc    120 gttgcggagg gtgcgctcag agggccgcgt cgtggctgca gcggctgctg ccgccgcagg    180
ggatctaata tcacctacct gtccctgtca ctcttgacac ttctctgtca gggctgccgc    240 gtggggggg ggcgggcaga gcgcggtcgg cgttagcttt ccttattgga ggggttcttg    300
ggggagggag ggagagaaga agggggtctt tgcccactct tgtttcgctt tggagcttgg    360
aagcctgctc cctaaagacg ctctgagtgg tgcccttctg cccacatccc atgtcttcgt    420
ttgcccgctg actttccgtc tccggacttt ttcgcttgag ccttccggag gagacgggg    480 cagcttggct tgagaactcg gcgggggttg cgtcccctgg ctctccccgc agcggggaaa    540
ctccgcgcct agagcgcgac ccggagcggg cagcggcggc tacgggggct cggcggggca    600
gtagccaagg actagtagag cgtcgcgctc cctcgtccat gaactgcatg aaaggcccgc    660
ttcacttgga gcaccgagca gcggggacca agctgtcggc cgtctcctca tcttcctgtc    720
accatcccca gccgttagcc atggcttcgg ttctggctcc cggtcagccc cggtcgctgg    780
actcctccaa gcacaggctg gaggtgcaca ccatctccga cacctccagc ccggaggccg    840
cagagaaaga taaaagccag caggggaaga atgaggacgt gggcgccgag gacccgtcta    900
agaagaagcg gcaaaggcgg cagcggactc actttaccag ccagcagctc caggagctgg    960
aggccacttt ccagaggaac cgctacccgg acatgtccac acgcgaagaa atcgctgtgt   1020
ggaccaacct tacggaagcc cgagtccggg tttggttcaa gaatcgtcgg gccaaatgga   1080
gaaagaggga gcgcaaccag caggccgagc tatgcaagaa tggcttcggg ccgcagttca   1140
```

```
atgggctcat gcagccctac gacgacatgt acccaggcta ttcctacaac aactgggccg    1200
ccaagggcct tacatccgcc tccctatcca ccaagagctt ccccttcttc aactctatga    1260
acgtcaaccc cctgtcatca cagagcatgt tttccccacc caactctatc tcgtccatga    1320
gcatgtcgtc cagcatggtg ccctcagcag tgacaggcgt cccgggctcc agtctcaaca    1380
gcctgaataa cttgaacaac ctgagtagcc cgtcgctgaa ttccgcggtg ccgacgcctg    1440
cctgtcctta cgcgccgccg actcctccgt atgtttatag ggacacgtgt aactcgagcc    1500
tggccagcct gagactgaaa gcaaagcagc actccagctt cggctacgcc agcgtgcaga    1560
acccggcctc caacctgagt gcttgccagt atgcagtgga ccggcccgtg tgagccgcac    1620
ccacagcgcc gggatcctag gaccttgccg gatggggcaa ctccgccctt gaaagactgg    1680
gaattatgct agaaggtcgt gggcactaaa gaaagggaga gaaagagaag ctatatagag    1740
aaaaggaaac cactgaatca agagagagc tcctttgatt tcaagggat gtcctcagtg      1800 tctgacatct ttcactacaa gtatttctaa cagttgcaag gacacataca caaacaaatg    1860
tttgactgga tatgacattt taacattact ataagcttgt tatttttaa gtttagcatt     1920 gttaacattt aaatgactga aaggatgtat atatatcgaa atgtcaaatt aattttataa    1980
aagcagttgt tagtaatatc acaacagtgt ttttaaaggt taggctttaa aataaagcat    2040
gttatacaga agcgattagg attttttcgct tgcgagcaag ggagtgtata tactaaatgc    2100
cacactgtat gtttctaaca tattattatt attataaaaa atgtgtgaat atcagttta      2160 gaatagtttc tctggtggat gcaatgatgt ttctgaaact gctatgtaca acctaccctg    2220
tgtataacat ttcgtacaat attattgttt tactttcag caaatatgaa acaaatgtgt     2280
tttatttcat gggagtaaaa tatactgcat acaaaaaaaa aaaaaaaaaa aaaaaaa      2337
```

<210> SEQ ID NO 2
<211> LENGTH: 324
<212> TYPE: PRT
<213> ORGANISM: Homo sapiens
<220> FEATURE:
<221> NAME/KEY: PEPTIDE
<222> LOCATION: (1)...(324)
<223> OTHER INFORMATION: Genbank accession No. NP_000316. Pituitary
      homeobox 2 isoform c

<400> SEQUENCE: 2

Met Asn Cys Met Lys Gly Pro Leu His Leu Glu His Arg Ala Ala Gly
1               5                   10                  15

Thr Lys Leu Ser Ala Val Ser Ser Ser Cys His His Pro Gln Pro
            20                  25                  30

Leu Ala Met Ala Ser Val Leu Ala Pro Gly Gln Pro Arg Ser Leu Asp
        35                  40                  45

Ser Ser Lys His Arg Leu Glu Val His Thr Ile Ser Asp Thr Ser Ser
    50                  55                  60

Pro Glu Ala Ala Glu Lys Asp Lys Ser Gln Gln Gly Lys Asn Glu Asp
65                  70                  75                  80

Val Gly Ala Glu Asp Pro Ser Lys Lys Lys Arg Gln Arg Arg Gln Arg
                85                  90                  95

Thr His Phe Thr Ser Gln Gln Leu Gln Glu Leu Glu Ala Thr Phe Gln
            100                 105                 110

Arg Asn Arg Tyr Pro Asp Met Ser Thr Arg Glu Glu Ile Ala Val Trp
        115                 120                 125

Thr Asn Leu Thr Glu Ala Arg Val Arg Val Trp Phe Lys Asn Arg Arg
    130                 135                 140

```
Ala Lys Trp Arg Lys Arg Glu Arg Asn Gln Gln Ala Glu Leu Cys Lys
145                 150                 155                 160

Asn Gly Phe Gly Pro Gln Phe Asn Gly Leu Met Gln Pro Tyr Asp Asp
                165                 170                 175

Met Tyr Pro Gly Tyr Ser Tyr Asn Asn Trp Ala Ala Lys Gly Leu Thr
            180                 185                 190

Ser Ala Ser Leu Ser Thr Lys Ser Phe Pro Phe Phe Asn Ser Met Asn
        195                 200                 205

Val Asn Pro Leu Ser Ser Gln Ser Met Phe Ser Pro Pro Asn Ser Ile
    210                 215                 220

Ser Ser Met Ser Met Ser Ser Ser Met Val Pro Ser Ala Val Thr Gly
225                 230                 235                 240

Val Pro Gly Ser Ser Leu Asn Ser Leu Asn Asn Leu Asn Asn Leu Ser
                245                 250                 255

Ser Pro Ser Leu Asn Ser Ala Val Pro Thr Pro Ala Cys Pro Tyr Ala
                260                 265                 270

Pro Pro Thr Pro Pro Tyr Val Tyr Arg Asp Thr Cys Asn Ser Ser Leu
            275                 280                 285

Ala Ser Leu Arg Leu Lys Ala Lys Gln His Ser Ser Phe Gly Tyr Ala
            290                 295                 300

Ser Val Gln Asn Pro Ala Ser Asn Leu Ser Ala Cys Gln Tyr Ala Val
305                 310                 315                 320

Asp Arg Pro Val

<210> SEQ ID NO 3
<211> LENGTH: 21
<212> TYPE: RNA
<213> ORGANISM: Artificial Sequence
<220> FEATURE:
<223> OTHER INFORMATION: Synthetic sequence miRNA inhibitor hsa-miR-106p

<400> SEQUENCE: 3
uaaagugcug acagugcaga u                                            21
```

METHOD FOR PROMOTING MUSCLE REGENERATION

STATEMENT REGARDING SEQUENCE LISTING

The Sequence Listing associated with this application is provided in text format in lieu of a paper copy, and is hereby incorporated by reference into the specification. The name of the text file containing the Sequence Listing is 920172 401USPC SEQUENCE LISTING.txt. The text file is 6.3 KB, was created on Aug. 15, 2019, and is being submitted electronically via EFS-Web.

TECHNICAL FIELD OF THE INVENTION

The present invention relates to the field of the biotechnology, in particular to use of the expression of miRNA-106b and/or of the Pitx2 gene for the treatment or prevention of muscular dystrophies.

PRIOR ART

The following discussion of the prior art of the invention is provided merely to aid the reading in understanding the invention.

Skeletal muscle has the ability to repair and regenerate due to the presence of resident stem cells, referred to as muscle satellite cells. In mature muscle tissue, satellite cells constitute a small, scattered population of mitotically and physiologically quiescent cells, marked by their expression of transcription factor Pax7 (FIG. 1). Adult muscle satellite stem cells are a cell line from embryonic myogenic progenitor cells Pax3/pax7+ which remain in adult muscle in a state of quiescence and after an injury they are activated, proliferate and enter the myogenic differentiation program due to the upregulation of myogenic determination genes myf5, MyoD and myogenin, thus forming new myoblasts that eventually fuse to one another to generate new muscle tissue (FIG. 1).

Muscular dystrophies are a group of genetic conditions characterized by progressive degenerative muscle disorders. One of the most serious characteristics of these pathologies consists of the gradual loss of skeletal muscle tissue due to chronic degeneration accompanied by deficient regeneration. Their most common forms in childhood are Duchenne muscular dystrophy (DMD) and Becker muscular dystrophy (BMD) and are characterized by being recessive hereditary disorders related to the chromosome X caused by dystrophin gene mutations. Dystrophin plays an important structural role in muscle fiber serving as a connection between the extracellular matrix and the cytoskeleton. The N-terminal region of this protein is bound to the cytoskeleton protein actin, whereas the C-terminal end is part of the dystrophin-associated glycoprotein complex (DGC) which connects with the membrane of the muscle fiber (sarcolemma). Without dystrophin, mechanical tension leads to ruptures in the sarcolemma, causing progressive muscular necrosis, loss of independent ambulation at the start of adolescence, cardiomyopathy, respiratory failure, and premature death in affected individuals.

Today there is no cure for muscular dystrophies, and existing therapies are ineffective. While it is likely that gene therapies will be able to provide a cure for these diseases, there are important obstacles that limit their application. Potential approaches have therefore been carried out, ranging from gene augmentation strategies using viral vectors or plasmids intended for restoring the expression of dystrophin, to gene upregulation, which could be used to overcome the lack of expression of the inactivated gene. Although some of these approaches have proven to be partially effective, the results obtained up until now have shown their numerous limitations. In particular, the progressive loss of expression of the therapeutic gene observed after treatment has clearly indicated that modification of mature fiber alone is not enough to maintain the beneficial effects obtained by this therapeutic approach.

Therefore, there is a need to provide new therapies that are effective in the treatment of muscular dystrophies, particularly by means of identifying new approaches for improving muscle regeneration in these patients.

DISCLOSURE OF THE INVENTION

The present invention solves the problem of providing new therapies that are effective in the treatment of muscular dystrophies through the use of compositions comprising a compound capable of:
a. increasing the expression of the Pitx2 gene in muscle satellite stem cells of a human or animal subject with respect to the expression observed in the absence of the compound in said cells; and/or
b. reducing the expression of miRNA-106b in muscle satellite stem cells of a human or animal subject with respect to the expression observed in the absence of the compound in said cells.

DETAILED DISCLOSURE OF THE INVENTION

Definitions

Figure 1:
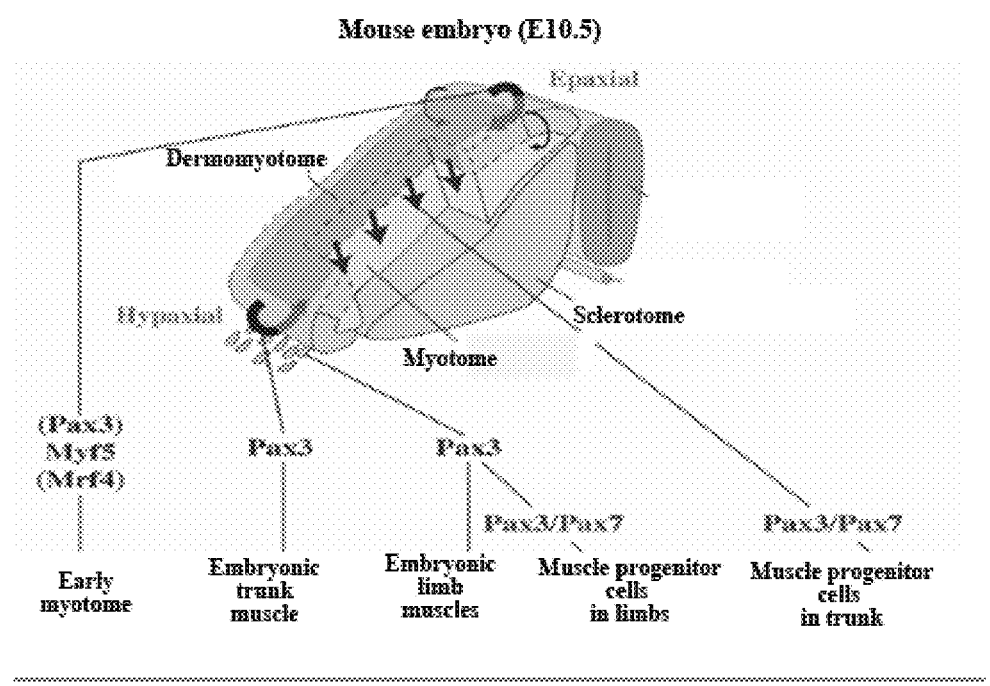
FIG. 1. Embryonic origin of the muscle satellite cells. (Buckingham and Vincent, Current Opinion in Genetics & Development, 2009)

As used in the specification and the attached claims, the term "muscle satellite stem cells" of a human or animal subject constitutes a small, scattered population of mitotically and physiologically quiescent cells, labeled by their expression of transcription factor Pax7 (FIG. 1). Adult muscle satellite stem cells are a line from embryonic myogenic progenitor cells Pax3/Pax7+ which remain in adult muscle in a state of quiescence and after an injury they are activated, proliferate and enter the myogenic differentiation program due to the upregulation of the myogenic determination genes myf5, MyoD and myogenin thus forming new myoblasts that eventually fuse to one another to generate new muscle tissue (FIG. 1). Preferably, the term "muscle satellite stem cells" refers to a cell located between the basal lamina and sarcolemma of skeletal muscle, preferably adult skeletal muscle, and marked by the expression of transcription factor Pax7, from a Pax3/pax7+ muscle progeny of embryonic myogenic progenitor cells.

As used in the specification and the attached claims, the term "miRNA-106b" preferably refers to the single-stranded RNA Ensembl:ENSG00000208036 MIM:612983; miRBase:MI0000734, or to a polynucleotide sequence of RNA having a nucleotide sequence identical by at least 90%, 92%, 94%, 96%, 98% or 99%, based on the identity of all the nucleotides of said sequence, to the nucleotide sequence Ensembl:ENSG00000208036 MIM:612983; miRBase: MI0000734, preferably, a polynucleotide sequence of RNA having a nucleotide sequence identical by at least 90%, 92%, 94%, 96%, 98% or 99%, based on the identity of all the nucleotides of said sequence, to the nucleotide sequence Ensembl:ENSG00000208036 MIM:612983; miRBase: MI0000734, and having the function of regulating the expression of other genes using the ribo-interference pathway.

As used in the specification and the attached claims, the term "miRNA inhibitor hsa-miR-106b-5p (ID: MH10067; Cat: 4464084, Ambion)" refers to a nucleotide sequence of SEQ ID NO:3, which is a single-strand RNA chemically modified and designed for specifically binding to and inhibiting endogenous molecules of miR-106b.

As used in the specification and the attached claims, the term "Pitx2 gene" is a member of the family of bicoid homeobox transcription factors which plays a relevant role in morphogenesis (reference polynucleotide sequence in Genbank with accession number NM_000325, identifying *Homo sapiens* paired-like homeodomain 2 (PITX2))

The term "increase" or "increasing" refers to increases above the basal level. For example, basal levels are normal at in vivo levels before, or in the absence of, the addition of an activating compound.

The term "reduction" or "reducing" or "inhibiting" or "inhibition" refers to reductions below the basal level. For example, basal levels are normal at in vivo levels before, or in the absence of, the addition of an inhibitory compound.

In this specification and in the claims that follow, reference will be made to a number of terms that are defined to have the following meanings:

"Optional" or "optionally" means that the described event or circumstance subsequently may or may not occur, and that the description includes cases in which said event or circumstance occurs and cases in which it does not.

As it is used herein, the terms "prevent", "preventing" and "prevention" refer to the methods for avoiding or impeding the development of a disease or disorder or delaying the recurrence or the onset of one or more symptoms of a disorder in a subject resulting from the administration of a prophylactic agent.

The term "pharmaceutically acceptable carrier" intends to include the formulation used to stabilize, solubilize and be mixed in some way with active ingredients that are administered to living animals, including human beings. This includes any and all solvents, dispersion media, coatings, antibacterial and antifungal agents, isotonic and absorption delaying agents, and the like, which are compatible with the pharmaceutical dosage form. Except where any conventional medium or agent is incompatible with the active compound, such use in compositions is contemplated.

As it is used herein, the term "disease" is generally intended to be synonymous to, and used interchangeably with the terms "disorder" and "condition" (as in medical condition), in that they all reflect an abnormal condition of the body or of one of its parts that jeopardizes normal functioning and typically presents through distinctive signs and symptoms.

The term "combination therapy" means the administration of two or more therapeutic agents for treating a therapeutic condition or disorder described in the present description. Said administration encompasses the co-administration of these therapeutic agents in a substantially simultaneous manner, such as in a single capsule having a set active ingredient ratio or in multiple individual capsules for each active ingredient. Furthermore, such administration also encompasses the sequential use of each type of therapeutic agent. In any case, the treatment regimen will provide beneficial effects from combining compounds in the treatment of conditions or disorders described in the present.

The expression "therapeutically effective" intends to describe the amount of active ingredients used in the treatment of a disease or disorder. This amount will be the amount necessary for achieving the objective of reducing or eliminating said disease or disorder.

The term "subject" refers to all mammals, including human beings. Examples of subjects include, but are not limited to, human beings, cows, dogs, cats, goats, sheep, pigs, and rabbits.

Throughout this application, reference is made to various publications. The descriptions of these publications are incorporated herein in their entirety by reference for the purpose of describing the state of the art to which it belongs more thoroughly. The described references are also individually and specifically incorporated herein as a reference because of the material contained therein, which is discussed in the phrase on which said reference is based.

DESCRIPTION OF THE INVENTION

The present invention deals with the problem of providing new therapies that are effective in the treatment of muscular dystrophies, increasing the ability of skeletal muscle stem cells to regenerate tissue that is lost as a result of the muscular dystrophy.

For this purpose the authors of the present invention have evaluated the contribution of the Pitx2 gene in the regulation of the tissue-specific transcription of different microRNAs during myogenesis. The analysis of gene expression profiles (microRNA-microarrays) in a myoblast cell line (Sol8 cell line) has led the authors of the present invention to identify a series of microRNAs (miRNAs) that are differentially regulated into Sol8 myoblasts overexpressing Pitx2 (see FIG. 2). The analysis of the effects of said microRNAs on myoblast proliferation and the identification of their supposed targets demonstrate that Pitx2 regulates a subset of microRNAs having a profound effect on myoblast cell cycle progression (miR15b, miR-23b, miR-106b and miR-503). Additionally, the authors of the invention found that this Pitx2-miRNA pathway also regulates cell proliferation in satellite cells isolated from mouse skeletal muscle (FIG. 1). These results indicate that Pitx2 acts by enlarging the satellite cell-derived myoblast population during regenerative myogenesis differentiation processes (FIG. 3).

Figure 3:
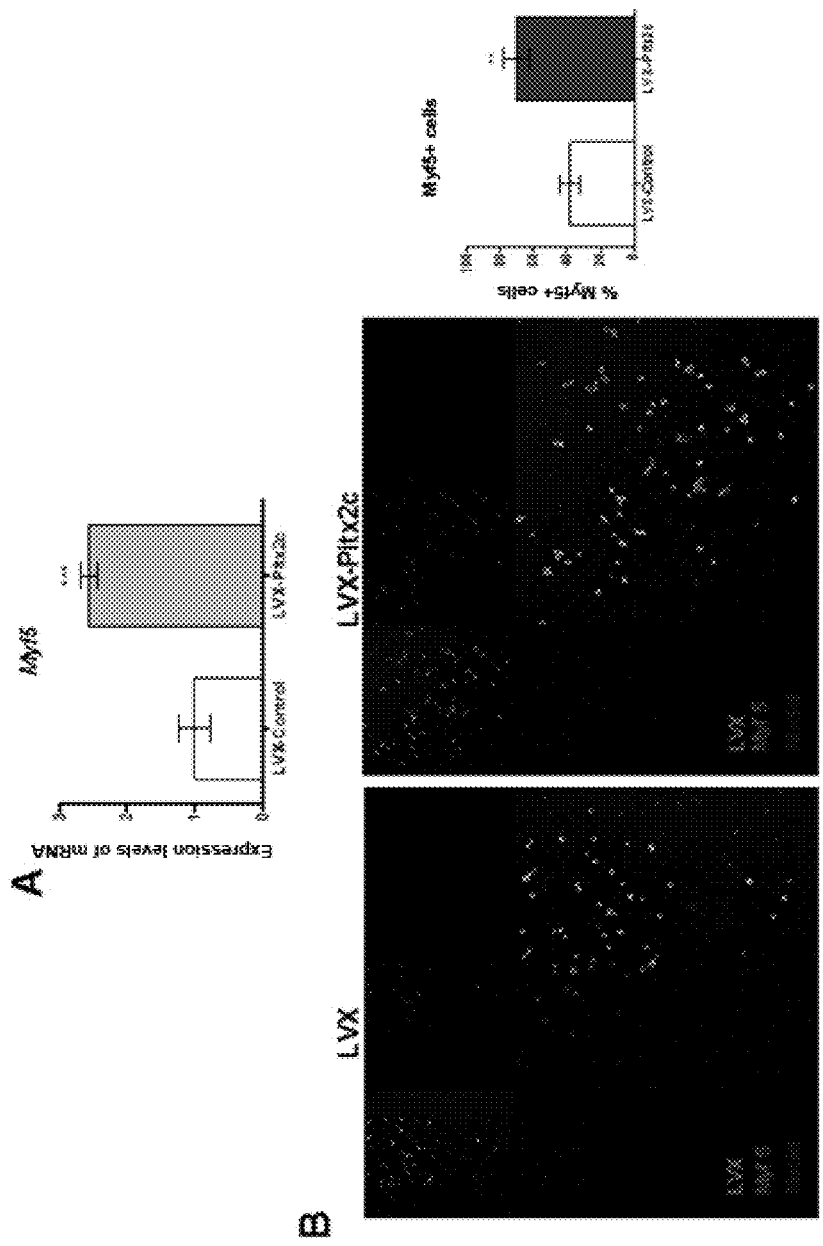
FIG. 3. A) Expression of Myf5 (qRT-PCR) increases in the satellite cells overexpressing Pitx2. B) Quantification by immunohistochemistry shows a significant increase in Myf5+ cells. C) Overexpression of miR-106b leads to a decrease in the expression of Myf5, validating it as a target of this miRNA. D) Normalized activity of the luciferase of Myf5 3'-UTR luciferase reporter (VVT Myf5 3'-UTR), with the empty plasmid (Vector) or co-transfecting with pre-miR-106b shows the loss of luciferase activity with the miR-106b. There is no loss of luciferase activity when the miR-106b seed sequence was mutated.
Figure 3:
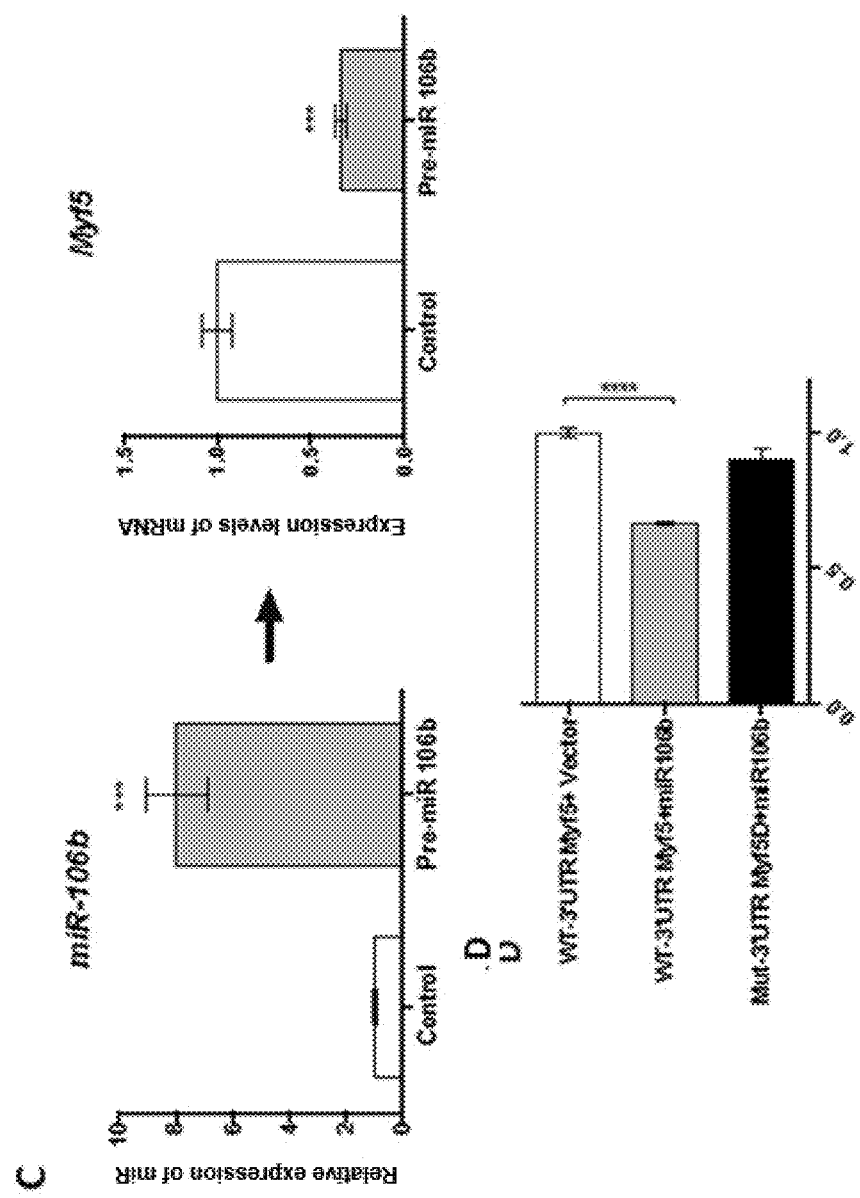
Figure 4:
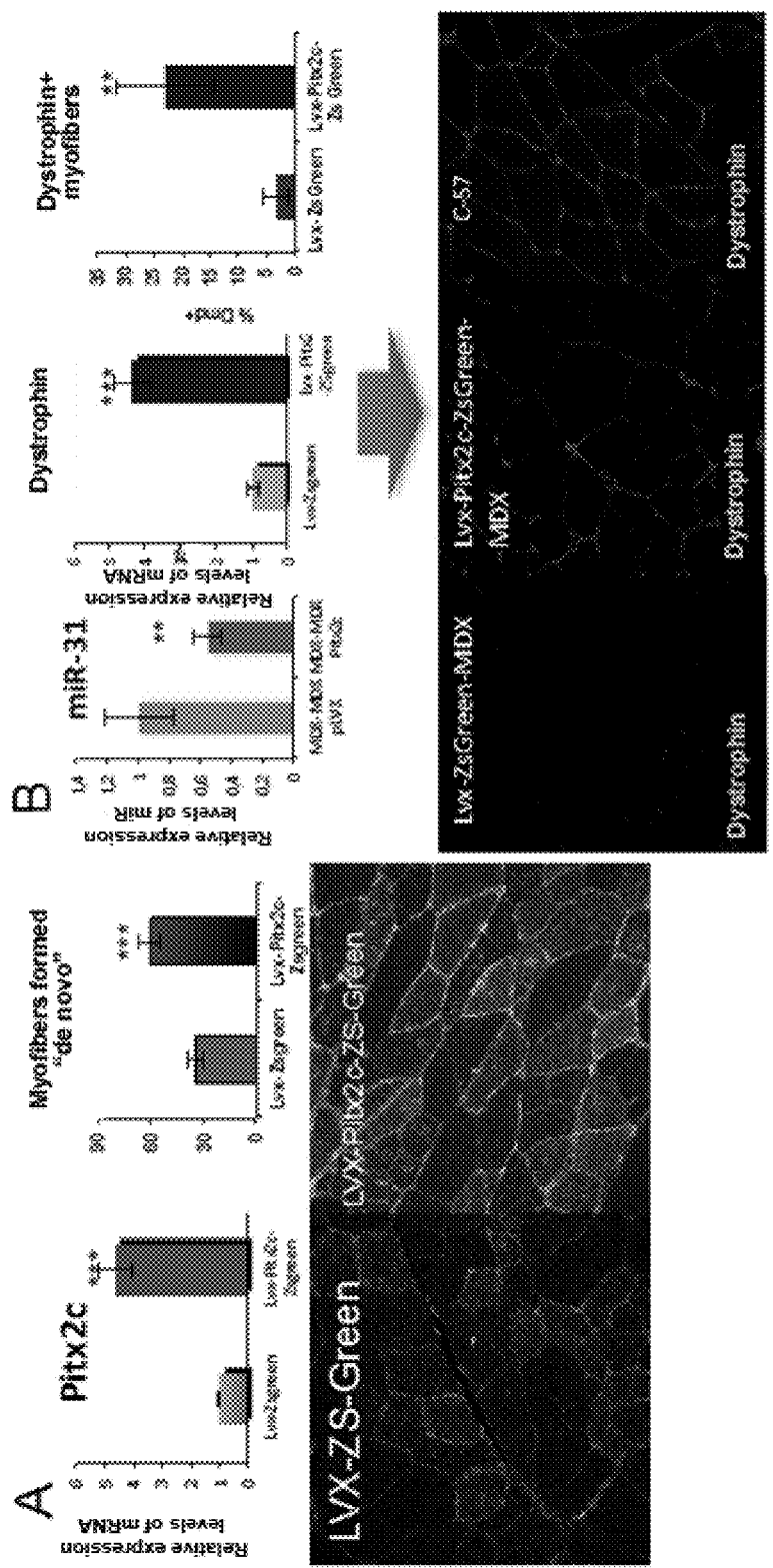
FIG. 4. A) qRT-PCR analysis of overexpression of Pitx2c in the MDX mouse muscles injected with dystrophic satellite cells transfected with lentiviral LVX-Pitx2c-ZS-Green vector compared to muscle injected with cells transfected with the empty lentivirus (LVX-ZS-Green vector); percentage of fibers formed "de novo" (ZS-Green+cells) in transplanted muscles after 15 days and representative image. B) Decrease in the expression of miR-31 in muscles transplanted with cells overexpressing Pitx2 leads to an increase in expression levels of dystrophin and to a significant increase in fibers expressing dystrophin. C) Treadmill test shows the functional improvement of DMDmdx mice injected with cells overexpressing Pitx2. D) Immunohistochemical analysis of cells in proliferation (Ki67+) 15 days after cell transplantation. E) qRT-PCR analysis of expression of miRNAs modulated by Pitx2 in the muscle of DMDmdx mice in which the cell transplantation was performed with cells overexpressing Pitx2. F) Expression levels of cyclins D1 and D2 and of transcription factor Myf5 were increased in muscles transplanted with cells overexpressing Pitx2, indicating that the Pitx2-miRNA molecular cascade is conserved in the "in vivo" transplantation system.
Figure 4:
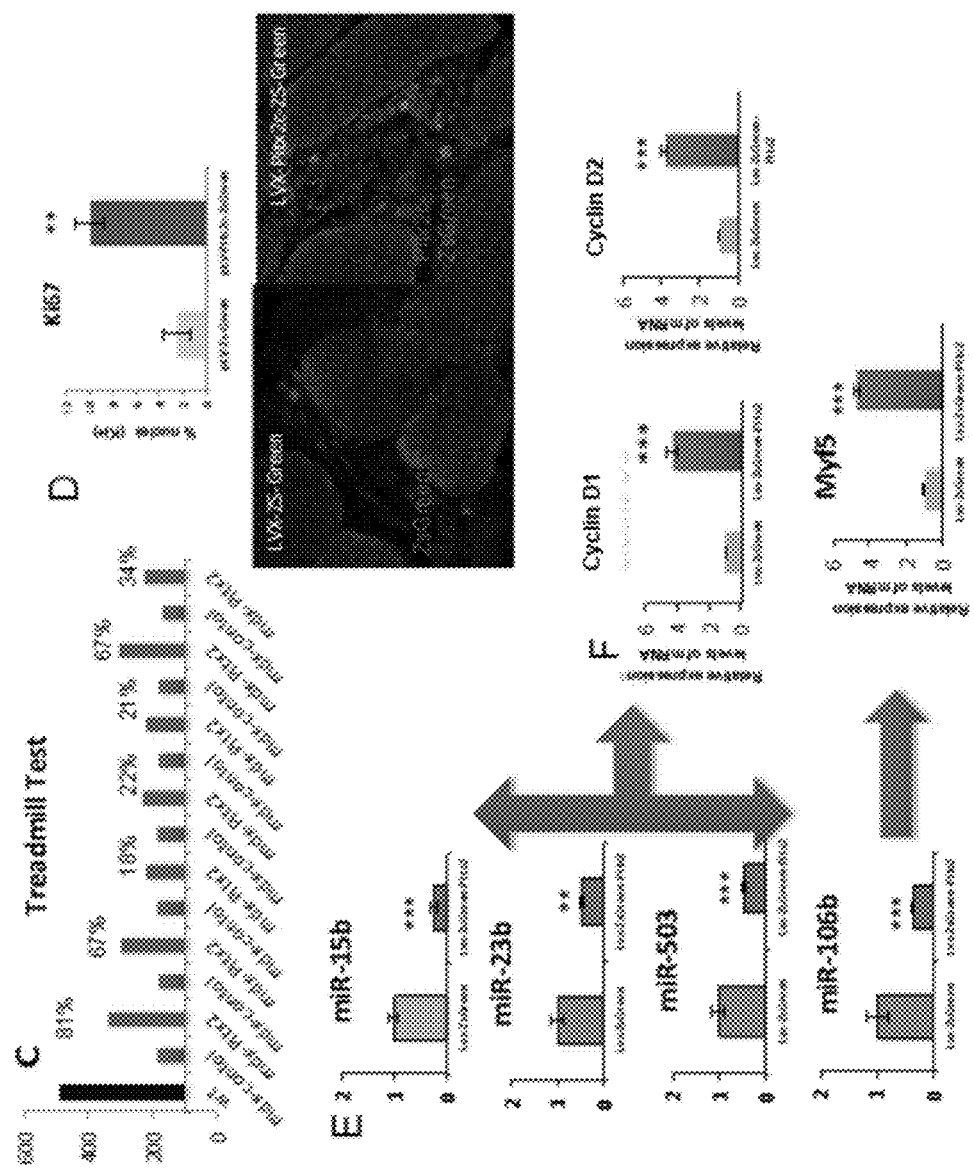
Figure 6:
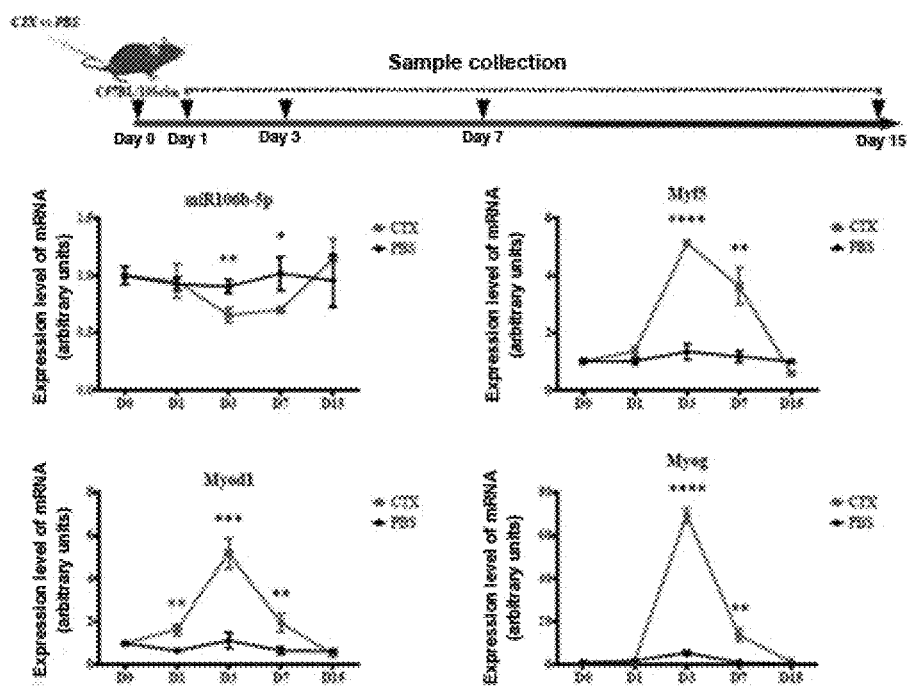
FIG. 6. Expression profiles for miR-106b, Myf5, MyoD and myogenin in tibialis anterior muscle after the injection of cardiotoxin in mice. D0-D15: days after the injection of cardiotoxin.
Figure 7:
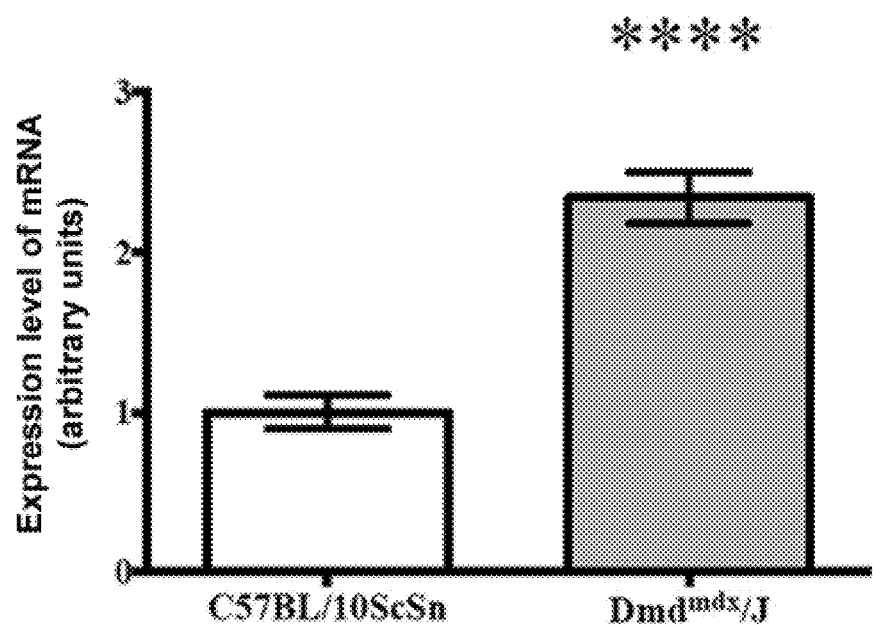
FIG. 7. miR-106b is regulated by an increase in DMD/mdx mice (n=6).
Figure 8:
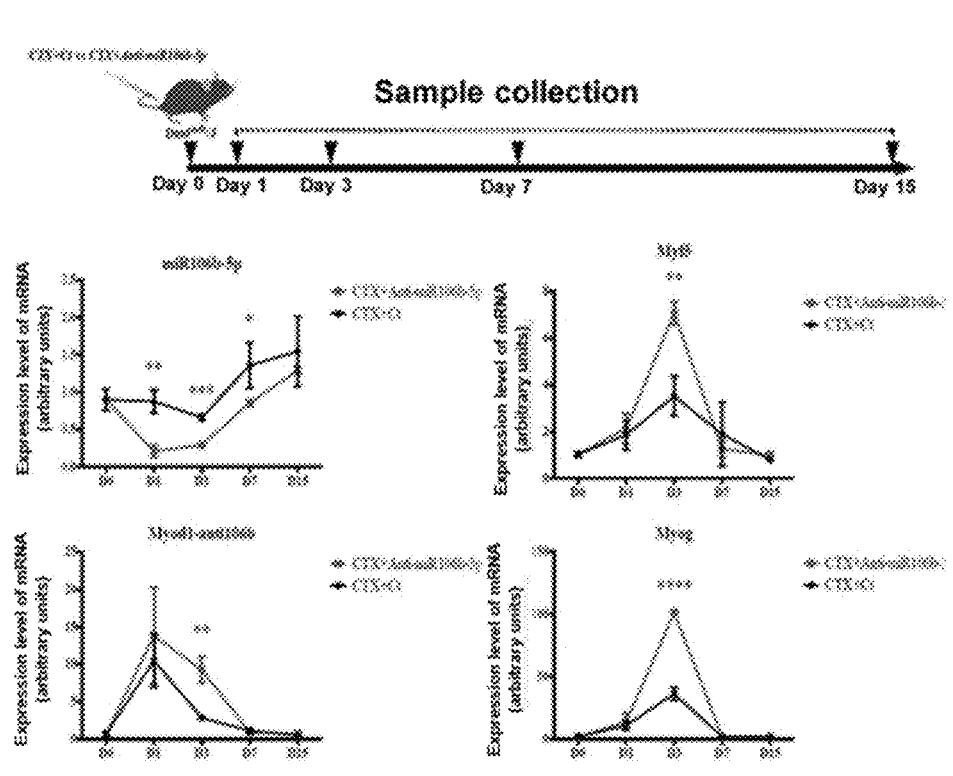
FIG. 8. Expression profiles for miR-106b, Myf5, MyoD and myogenin in tibialis anterior muscle after the injection of anti-miR106b compound (miRNA inhibitor) in TA muscle in mice. D0-D15: days after the injection of anti-miR compound.

Additionally, these results demonstrate that reducing the expression of miRNA-106b in muscle satellite stem cells of a human or animal subject with respect to the expression observed in the absence of the compound in said cells enlarges the satellite cell-derived myoblast population during regenerative myogenesis differentiation processes (see FIGS. 3 and 4). Furthermore, the results clearly show that miR-106b is down-regulated during the time interval comprised between days 3 and 7 after the injection of cardiotoxin (FIG. 6). Curiously, as shown in the examples, on day 3 from the injection of the antimiR-106b compound, a clear upregulation of Myf5, MyoD and myogenin was found, supporting the notion that downregulation in miR-106b is required for suitable myogenic differentiation during the muscle regeneration process (FIG. 6). Furthermore, to further study the role of miR-106b during muscle repair, it was investigated whether the expression of miR-106b changed in a context in which muscle regeneration is not completed satisfactorily, such as in DMD (Duchenne muscular dystrophy). In this sense, it was demonstrated that the expression of miR-106b clearly increases in MDX mouse muscles, an animal model that is widely used for human DMD (FIG. 7). Therefore, it was then considered whether muscle regeneration could be modulated in dystrophic mice by decreasing the expression of miR-106b. To approach this issue, a strategy was developed by means of which cardiotoxin and miRNA inhibitor hsa-miR-106b-5p (ID: MI-110067; Cat: 4464084, Ambion) (SEQ ID NO:3) were injected in TA muscle (tibialis anterior muscle) of 4 month old MDX mice (1.7 nmol per injection). After the injection of miRNA inhibitor, the muscles were removed 1, 3 and 15 days after the injection of anti-miR-106b compound for analysis. The results clearly show that the injection of anti-miR-106b compound can decrease the presence of miR-106b. Interestingly enough, as shown in the examples the decrease in miR-106b coincides with myogenic differentiation waves as observed by means of upregulation of Myf5, MyoD and myogenin, which indicates that decreased levels of miR-106b induced by means of injection of anti-miR106b compound can boost muscle differentiation (FIG. 8).

Figure 11:
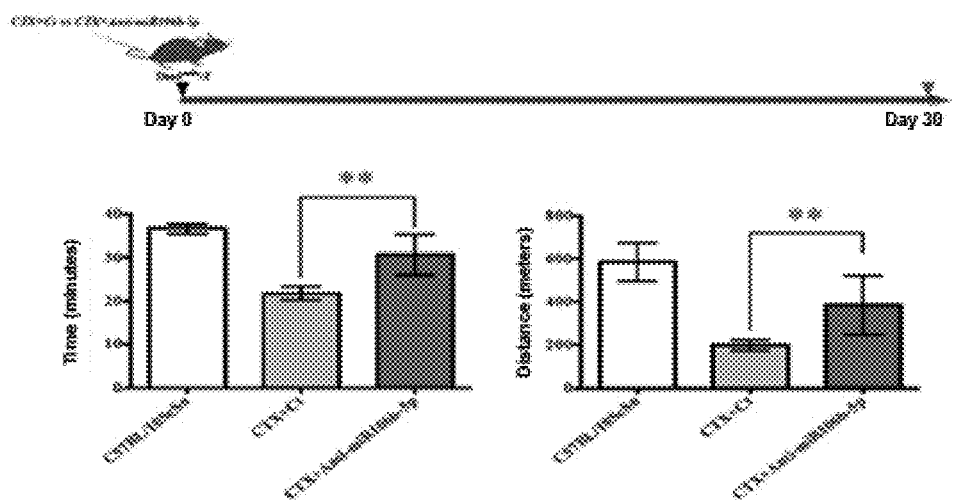
FIG. 11. Analysis of functional recovery by means of treadmill test: note that distance and time improved significantly in DMD/mdx mice injected with anti-miR-106b compound (n=6).

Finally, treadmill tests to exhaustion were conducted in DMD/mdx mice injected with anti-miR106b compound 30 days after treatment with anti-miR-106b compound. As illustrated in FIG. 11, running time and distance were from 50% to 95% higher, respectively, in mice treated with anti-miR-106b compound with respect to the control, which indicates that the injection of anti-miR-106b compound strengthens physical performance.

When considered together, the results showed that miR-106b plays a key role during the muscle regeneration process in mice. Furthermore, the data herein presented demonstrated that the intramuscular injection of anti-miR-106b compound can improve the ability of regeneration in DMD mice.

Accordingly, a first aspect of the present invention relates to the use of a composition (hereinafter "composition of the present invention") comprising a compound capable of increasing the expression of the Pitx2 gene, activating compound, in muscle satellite stem cells of a human or animal subject with respect to the expression observed in the absence of the compound in said cells; and/or reducing the expression of miRNA-106b, inhibitory compound, in muscle satellite stem cells of a human or animal subject with respect to the expression observed in the absence of the compound in said cells;

for preparing a drug for promoting muscle regeneration.

Alternatively, the first aspect of the invention relates to a composition comprising a compound capable of increasing the expression of the Pitx2 gene, activating compound, in muscle satellite stem cells of a human or animal subject with respect to the expression observed in the absence of the compound in said cells; and/or reducing the expression of miRNA-106b, inhibitory compound, in muscle satellite stem cells of a human or animal subject with respect to the expression observed in the absence of the compound in said cells;

for use in promoting muscle regeneration.

"Increasing the expression of the Pitx2 gene" is understood as the increase with respect to the baseline, or compared to a control, by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, or 2, 3, 4, 5, 6, 7, 8, 9, 10, 11, 12, 13, 14, 15, 20, 25, 30, 35, 40, 45, 50, or more times.

The activating compounds can be identified by means of a screening method that allows identifying in a compound the ability of activating Pitx2, which comprises putting a cell, preferably a muscle satellite stem cell, in contact with a compound suspected of being able to activate Pitx2; testing the content of the cells to determine the amount and/or biological activity of Pitx2 and to compare the determined amount and/or biological activity of Pitx2 with a pre-determined level, in which a change in said amount and/or biological activity of Pitx2 is indicative of a compound activating Pitx2. In a preferred embodiment, detection is performed by means of real-time quantitative RT-PCR using primers specific for each isoform.

In the context of the present invention, muscle satellite stem cells are understood as stem cells, or muscle pre-cells, which serve to aid the regeneration of adult skeletal muscle. As a result of proliferation (when the satellite cells are activated) and subsequent differentiation (when they start to express transcription factors that commit them to a myogenic (myoblast) line), the satellite cells fuse to one another or with adjacent damaged muscle fibers, which increases the number of myonueclei in fibers for growth and repair. Satellite cell activation and proliferation is necessary for the purpose of meeting the needs of forming new muscle fibers to regenerate muscle. The differentiation is necessary so that satellite cells can first be converted to myoblasts and to fibers after the fusion process.

A preferred embodiment of the first aspect of the invention relates to the use of the composition of the invention, where said drug is used for promoting muscle regeneration in the treatment of a dystrophinopathy or dystrophy, preferably, where said dystrophinopathy or dystrophy is selected from the list consisting of Duchenne muscular dystrophy and Becker muscular dystrophy.

Another preferred embodiment of the first aspect of the invention or of any of its preferred embodiments relates to the use of the composition of the invention, where said compound, activating compound, is a polynucleotide of DNA (hereinafter polynucleotide of the invention) comprising a sequence selected from the list consisting of:
the polynucleotide sequence in Genbank with accession number NM_000325, or its complementary sequence;
a sequence selectively hybridizing with the sequence of (a); and
a polynucleotide sequence of DNA coding for an amino acid sequence identical by at least 90%, 92%, 94%, 96%, 98% or 99% based on the identity of all the amino acids of said sequence, to the amino acid sequence in Genbank with accession number NP_000316.

In the context of the present invention, the polynucleotide sequence in Genbank with accession number NM_000325 (SEQ ID NO 1) is identified as *Homo sapiens* paired-like homeodomain 2 (PITX2), transcript variant 3, mRNA. Said nucleotide sequence is provided below:

```
GTTAGGCCAACAGGGAAGCGCGGAGCCGCAGATCTGGTCCGTCGCTCGCC
TGGGTGCCTGGAGCTGAGCTGCGGCAAGGCCCGGCTCCTGTTCGACCGCC
CGAGGGGTGTGCGTGTGCGCGTTGCGGAGGGTGCGCTCAGAGGGCCGCGT
CGTGGCTGCAGCGGCTGCTGCCGCCGCAGGGGATCTAATATCACCTACCT
GTCCCTGTCACTCTTGACACTTCTCTGTCAGGGCTGCCGCGTGGGGGGGG
GGCGGGCAGAGCGCGGTCGGCGTTAGCTTTCCTTATTGGAGGGGTTCTTG
GGGGAGGGAGGGAGAGAAGAAGGGGGTCTTTGCCCACTCTTGTTTCGCTT
TGGAGCTTGGAAGCCTGCTCCCTAAAGACGCTCTGAGTGGTGCCCTTCTG
CCCACATCCCATGTCTTCGTTTGCCCGCTGACTTTCCGTCTCCGGACTTT
TTCGCTTGAGCCTTCCGGAGGAGACGGGGGCAGCTTGGCTTGAGAACTCG
GCGGGGGTTGCGTCCCCTGGCTCTCCCCGCAGCGGGGAAACTCCGCGCCT
AGAGCGCGACCCGGAGCGGGCAGCGGCGGCTACGGGGGCTCGGCGGGGCA
GTAGCCAAGGACTAGTAGAGCGTCGCGCTCCCTCGTCCATGAACTGCATG
AAAGGCCCGCTTCACTTGGAGCACCGAGCAGCGGGGACCAAGCTGTCGGC
CGTCTCCTCATCTTCCTGTCACCATCCCCAGCCGTTAGCCATGGCTTCGG
TTCTGGCTCCCGGTCAGCCCCGGTCGCTGGACTCCTCCAAGCACAGGCTG
GAGGTGCACACCATCTCCGACACCTCCAGCCCGGAGGCCGCAGAGAAAGA
TAAAAGCCAGCAGGGGAAGAATGAGGACGTGGGCGCCGAGGACCCGTCTA
AGAAGAAGCGGCAAAGGCGGCAGCGGACTCACTTTACCAGCCAGCAGCTC
CAGGAGCTGGAGGCCACTTTCCAGAGGAACCGCTACCCGGACATGTCCAC
ACGCGAAGAAATCGCTGTGTGGACCAACCTTACGGAAGCCCGAGTCCGGG
TTTGGTTCAAGAATCGTCGGGCCAAATGGAGAAAGAGGGAGCGCAACCAG
CAGGCCGAGCTATGCAAGAATGGCTTCGGGCCGCAGTTCAATGGGCTCAT
GCAGCCCTACGACGACATGTACCCAGGCTATTCCTACAACAACTGGGCCG
CCAAGGGCCTTACATCCGCCTCCCTATCCACCAAGAGCTTCCCCTTCTTC
AACTCTATGAACGTCAACCCCCTGTCATCACAGAGCATGTTTTCCCCACC
CAACTCTATCTCGTCCATGAGCATGTCGTCCAGCATGGTGCCCTCAGCAG
TGACAGGCGTCCCGGGCTCCAGTCTCAACAGCCTGAATAACTTGAACAAC
CTGAGTAGCCCGTCGCTGAATTCCGCGGTGCCGACGCCTGCCTGTCCTTA
CGCGCCGCCGACTCCTCCGTATGTTTATAGGGACACGTGTAACTCGAGCC
TGGCCAGCCTGAGACTGAAAGCAAAGCAGCACTCCAGCTTCGGCTACGCC
AGCGTGCAGAACCCGGCCTCCAACCTGAGTGCTTGCCAGTATGCAGTGGA
CCGGCCCGTGTGAGCCGCACCCACAGCGCCGGGATCCTAGGACCTTGCCG
GATGGGCAACTCCGCCCTTGAAAGACTGGGAATTATGCTAGAAGGTCGT
GGGCACTAAAGAAAGGGAGAGAAAGAGAAGCTATATAGAGAAAAGGAAAC
CACTGAATCAAAGAGAGAGCTCCTTTGATTTCAAAGGGATGTCCTCAGTG
TCTGACATCTTTCACTACAAGTATTTCTAACAGTTGCAAGGACACATACA
CAAACAAATGTTTGACTGGATATGACATTTTAACATTACTATAAGCTTGT
TATTTTTTAAGTTTAGCATTGTTAACATTTAAATGACTGAAAGGATGTAT
ATATATCGAAATGTCAAATTAATTTTATAAAAGCAGTTGTTAGTAATATC
ACAACAGTGTTTTAAAGGTTAGGCTTTAAAATAAAGCATGTTATACAGA
AGCGATTAGGATTTTTCGCTTGCGAGCAAGGGAGTGTATATACTAAATGC
CACACTGTATGTTTCTAACATATTATTATTATTATAAAAAATGTGTGAAT
```

-continued
```
ATCAGTTTTAGAATAGTTTCTCTGGTGGATGCAATGATGTTTCTGAAACT

GCTATGTACAACCTACCCTGTGTATAACATTTCGTACAATATTATTGTTT

TACTTTTCAGCAAATATGAAACAAATGTGTTTTATTTCATGGGAGTAAAA

TATACTGCATACAAAAAAAAAAAAAAAAAAAAAAAAA
```

In the context of the present invention, the amino acid sequence with accession number NP_000316 (SEQ ID NO 2) is identified as pituitary homeobox 2 isoform c [*Homo sapiens*]. Said amino acid sequence is provided below:

```
MNCMKGPLHLEHRAAGTKLSAVSSSSCHHPQPLAMASVLAPGQPRSLDSS

KHRLEVHTISDTSSPEAAEKDKSQQGKNEDVGAEDPSKKKRQRRQRTHFT

SQQLQELEATFQRNRYPDMSTREEIAVWTNLTEARVRVWFKNRRAKWRKR

ERNQQAELCKNGFGPQFNGLMQPYDDMYPGYSYNNWAAKGLTSASLSTKS

FPFFNSMNVNPLSSQSMFSPPNSISSMSMSSSMVPSAVTGVPGSSLNSLN

NLMNLSSPSLNSAVPTPACPYAPPTPPYVYRDTCNSSLASLRLKAKQHSS

FGYASVQNPASNLSACQYAVDRPV
```

In the context of the present invention, the degree of identity of an amino acid sequence is based on the identity of all the amino acids of said sequence.

In this embodiment of the invention, synthetic or modified nucleotides can be included among the polynucleotides of the invention. A number of different polynucleotide modification types are known in the art. These include methylphosphate and phosphorothioate main chains, addition of acridine or polylysine chains at the 3' and 5' ends of the molecule. For the purposes of the present invention, it must be understood that the polynucleotides described herein can be modified by any method available in the art.

The polynucleotides according to the invention can be produced in a recombinant manner, in a synthetic manner or by means available for the persons skilled in the art. They can also be cloned by standard techniques. The polynucleotides are typically provided in an isolated and/or purified form.

Another preferred embodiment of the first aspect of the invention or of any of its preferred embodiments relates to the use of the composition of the invention, where the compound is a polynucleotide of DNA comprising a sequence selected from the list consisting of the polynucleotide sequence with accession number NM_000325 (SEQ ID NO 1), or its complementary sequence or a polynucleotide sequence coding for an amino acid sequence identical by at least 99%, based on the identity of all the amino acids of said sequence, to the amino acid sequence with accession number NP_000316.

In an additional preferred aspect of the invention, the polynucleotides of the invention, such as those described above, can be transported, without degradation, by plasmid or viral vectors including an promoter of expression of the nucleic acid in the cells in which is delivered.

Therefore, in an additional embodiment of the invention, the activating compounds of the invention can comprise any of the polynucleotides of the invention described above or a plasmid or a vector capable of transporting or delivering said polynucleotides, preferably by means of a viral vector.

The viral vectors are, for example, adenoviruses, adeno-associated viruses, herpes virus, vaccinia virus, polio virus, AIDS virus, neuronal trophic virus, Sindbis virus and other RNA viruses, including viruses with the structure of HIV. Viral families sharing the properties of these viruses, making them suitable for use as vectors, are also preferred. Retroviruses are Moloney murine leukemia virus, MMLV, and retroviruses expressing the desirable properties of MMLV as a vector. Retroviral vectors are capable of carrying a larger genetic payload, i.e., a marker gene or transgene, than other viral vectors, and for this reason they are commonly used. However, they are not as useful in non-proliferative cells. Adenovirus vectors are relatively stable and easy to work with, have high titrations and can be sent in an aerosol formulation, and they can transfect cells that do not divide. Smallpox viral vectors are large and have several sites for gene insertion, are heat-stable and can be stored at room temperature. A preferred embodiment is a viral vector that has been designed for the purpose of suppressing the immune response of the host organism, caused by viral antigens.

The activating compounds can comprise, in addition to the described polynucleotides of the invention, plasmids or vectors or the peptides of the invention, for example, lipids such as liposomes, such as cationic liposomes (for example, DOTMA, DOPE, DC-cholesterol) or anionic liposomes.

The liposomes can further comprise proteins to facilitate cell-targeting in particular, if desired. The administration of a composition comprises a compound and a cationic liposome which can be administered in blood flowing into a target organ. Furthermore, the activator can be administered as a component of a microcapsule which can target specific cells types, such as cardiomyocytes, or where diffusion of the compound or administration of the compound of the microcapsule is designed for a specific type or dose.

Therefore, another preferred embodiment of the first aspect of the invention or of any of its preferred embodiments relates to the use of the composition of the invention, in which said compound is a vector or plasmid capable of transporting or delivering the sequence of polynucleotides, as defined in the context of the present invention, to muscle satellite stem cells. Preferably, said vector is a viral vector coding for the sequence of polynucleotides as defined above. More preferably, said viral vector is selected from the list consisting of adenoviral, lentiviral, retroviral and adeno-associated vectors.

Another preferred embodiment of the first aspect of the invention or of any of its preferred embodiments relates to the use of the composition of the invention, in which said drug comprises muscle satellite stem cells of a human or animal subject treated, transformed, transfected or transduced with the compound defined in the first aspect of the invention or in any of its preferred embodiments. Preferably, said cells treated, transformed, transfected or transduced with the compound are autologous cells. More preferably, said cells transformed, transfected or transduced with the compound are muscle satellite stem cells of a human subject suffering from a dystrophinopathy or a dystrophy.

In addition and as discussed above, reducing the expression of miRNA-106b in muscle satellite stem cells of a human or animal subject with respect to the expression observed in the absence of the compound in said cells enlarges the satellite cell-derived myoblast population during regenerative myogenesis differentiation processes. It is important to specify that said reduction must take place in muscle satellite stem cells of a human or animal subject, i.e., in those cells located between the basal lamina and the sarcolemma of skeletal muscle labeled by the expression of transcription factor Pax7 and from a Pax3/pax7+ muscle progeny of embryonic myogenic progenitor cells. To that end, the therapy must seek to achieve that objective, i.e., the therapy must allow the effective reduction of the levels of miRNA-106b in said cells.

Accordingly, a second aspect of the present invention relates to a composition comprising a compound, inhibitory compound, capable of reducing the expression of miRNA-106b in muscle satellite stem cells of a human or animal subject with respect to the expression observed in the absence of the compound in said cells, for preparing a drug for promoting muscle regeneration.

In the context of the present invention, "inhibiting or reducing the expression of miRNA-106b" is understood as the reduction with respect to the baseline, or compared to a control, by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, or 2, 3, 4, 5, 6, 7, 8, 9, 10, 11, 12, 13, 14, 15, 20, 25, 30, 35, 40, 45, 50, or more times.

The inhibitory compounds can be identified by means of a screening method that allows identifying in a compound the ability of inhibiting or reducing the intracellular expression of miRNA-106b, which comprises putting a cell, preferably a muscle satellite stem cell, in contact with a compound suspected of being able to inhibit or reduce the expression of miRNA-106b; testing the content of the cells to determine the amount and/or biological activity of the expression of miRNA-106b and to compare the determined amount and/or biological activity of miRNA-106b with a predetermined level, in which a change in said amount and/or biological activity of the expression of miRNA-106b is indicative of a compound with the ability to inhibit or reduce the intracellular expression of miRNA-106b. In a preferred embodiment, detection is performed by means of real-time quantitative RT-PCR.

In a preferred embodiment of the second aspect of the invention or of any of its preferred embodiments, said compound is an interfering RNA (siRNA) of miRNA-106b, such as an antisense RNA oligonucleotide of miRNA-106b or a polynucleotide expressing said antisense oligonucleotide. Preferably, said compound is a synthetic antisense RNA oligonucleotide of miRNA-106b which optionally has modifications for increasing its resistance to nucleases. More preferably, said compound is the miRNA inhibitor hsa-miR-106b-5p ID: MH10067; Cat: 4464084, Ambion, (SEQ ID NO:3) or a polynucleotide capable of inhibiting hsa-miR-106b-5p and having a nucleotide sequence identical by at least 90%, 92%, 94%, 96%, 98% or 99%, based on the identity of all the nucleotides of said sequence, to nucleotide sequence ID: MH10067; Cat: 4464084, Ambion (SEQ ID NO:3). More preferably, said compound is comprised in a vector or plasmid capable of transporting or delivering said compound to the muscle satellite stem cells, such as a viral vector, for example, adenoviral, lentiviral, retroviral and adeno-associated vectors.

In yet another preferred embodiment of the second aspect of the invention or of any of its preferred embodiments, said composition comprises muscle satellite stem cells of a human or animal subject treated, transformed, transfected or transduced with a compound capable of reducing the expression of miRNA-106b in said cells. Preferably, said cells treated, transformed, transfected or transduced with the compound are autologous cells. More preferably, said cells transformed, transfected or transduced with the compound are muscle satellite stem cells of a human or animal subject suffering from a dystrophinopathy or a dystrophy.

In another preferred embodiment of the second aspect of the invention or of any of its preferred embodiments, said drug is used for promoting muscle regeneration in the treatment of a dystrophinopathy.

In another preferred embodiment of the second aspect of the invention or of any of its preferred embodiments, said dystrophy or dystrophinopathy is selected from the list consisting of Duchenne muscular dystrophy and Becker muscular dystrophy.

It must be noted that the compositions described in the second aspect of the invention or in any of its preferred embodiments can be administered in the form of pharmaceutical composition comprising the compounds of this invention together with a pharmaceutically acceptable carrier or diluent. The compounds of this invention can thereby be administered in any conventional oral, parenteral, intramuscular or transdermal dosage form provided that said dosage forms are capable of transporting and delivering any of the compounds described in the second aspect of the invention to muscle satellite stem cells.

The composition of the second aspect of this invention can also be administered in a controlled release formulation, such as a slow release or a rapid release formulation. Such dosed controlled release formulations of the combination of the invention can be prepared using methods well known by the persons skilled in the art. The preferred method of administration will be determined by the physician in charge of the patient or another person skilled in the art after an evaluation of the subject's conditions and needs.

For parenteral administration purposes, nanoemulsions or solutions comprising nanoparticles or liposomes can be used. Said nanoemulsions or solutions can be suitably buffered. These aqueous solutions are particularly suitable for intravenous, intramuscular, subcutaneous and intraperitoneal injection purposes. In any case, methods of preparing various pharmaceutical compositions that can contain or comprise the inhibitory compound of the second aspect of the invention for administration in vivo in a pharmaceutically acceptable carrier are well known, as illustrated below in the description.

Preferably, said dystrophy or dystrophinopathy is treated by means of intramuscular administration, more preferably through intramuscular administration in the lower limbs of a human or animal subject. More preferably, the dystrophy or dystrophinopathy is treated by means of an intramuscular administration, more preferably by means of an intramuscular administration in the lower limbs of a human or animal subject, using as the compound an interfering RNA (siRNA) of miRNA-106b as an antisense RNA oligonucleotide of miRNA-106b or a polynucleotide expressing said antisense oligonucleotide, preferably using a synthetic antisense RNA oligonucleotide of miRNA-106b which optionally has modifications for increasing its resistance to nucleases, more preferably using the miRNA inhibitor hsa-miR-106b-5p ID: MI-110067; Cat: 4464084, Ambion (SEQ ID NO:3), or a polynucleotide capable of inhibiting hsa-miR-106b-5p and having a nucleotide sequence identical by at least 90%, 92%, 94%, 96%, 98% or 99%, based on the identity of all the nucleotides of said sequence, to nucleotide sequence ID: MI-110067; Cat: 4464084 (SEQ ID NO:3).

Finally, a third aspect of the invention relates to a screening method for screening a compound capable of promoting muscle regeneration comprising:
1. Selecting compounds from a library of compounds;
2. Testing if any of said compounds is capable of:
   a. increasing the expression of the Pitx2 gene in muscle satellite stem cells of a human or animal subject with respect to the expression observed in the absence of the compound in said cells; and/or
   b. reducing the expression of miRNA-106b in muscle satellite stem cells of a human or animal subject with respect to the expression observed in the absence of the compound in said cells; and
3. Selecting that compound or those compounds capable of carrying out that mentioned in any of the preceding paragraphs.

In the context of the present invention, the polynucleotides of DNA of the invention, such as those described above, that are delivered to the cells can be integrated in the host cell genome, normally through integration sequences. These sequences are often related to viral sequences, particularly in systems based on viruses when they are used. These viral integration systems can also be incorporated in the nucleic acids that will be delivered using an addition system of a non-nucleic acid-based delivery, said non-nucleic acid being a liposome, for example, such that the nucleic acid contained in the delivery system can be integrated in the host genome.

Other general techniques for integrating the host genome include, for example, systems designed for promoting homologous recombination with the host genome. These systems are typically based on the nucleic acid flanking sequence to be expressed having sufficient homology with a target sequence in the host cell genome where recombination between the nucleic acid vector and the target nucleic acid takes place, meaning that the delivered nucleic acid is integrated in the host genome. These systems and the methods required for promoting homologous recombination are known by persons skilled in the art.

The activating or inhibitory compounds described in the present specification can be administered in a pharmaceutically acceptable carrier and can be sent to the cells of the subject in vivo and/or ex vivo by means of a range of mechanisms well known in the art, as discussed above.

If ex vivo methods are used, the cells or tissues can be removed and kept outside the body according to standard protocols well known in the art. The activating or inhibitory compounds can be introduced in cells through any gene transfer mechanism, such as, for example, calcium phosphate-mediated gene delivery, electroporation, microinjection or proteoliposomes. Transduced cells can then be infused (for example, in a pharmaceutically acceptable carrier) or be homotopically transplanted in the subject by standard methods for the cell or tissue type. Standard methods are known for the transplant or infusion of several cells in a subject.

The activating or inhibitory compounds of the present invention can be used together with other treatment methods.

Furthermore, the present specification provides a method for increasing or improving the clinical status and the perceived well-being of a subject with dystrophy or with a dystrophinopathy, which comprises administering to subject in need of same an effective amount of an activating inhibitory compound, which increases or improves the clinical status of the subject treated for a certain period of time.

Current treatment methods also include a method for increasing the efficacy of other agents proposed for the same disease, which comprises administering to a subject in need of same an effective amount of an activating or inhibitory compound, and, optionally, a pharmaceutically acceptable carrier, thereby increasing the efficacy of the other agent or agents.

In any case, the compositions comprising the activating or inhibitory compound can be administered in vivo in a pharmaceutically acceptable carrier. "Pharmaceutically acceptable" is understood to be a material that is not biologically, or otherwise undesirable, i.e., the material can be administered to a subject, together with the nucleic acid or vector, without causing any undesirable biological effect or without harmfully interacting with any of the other components of the pharmaceutical composition in which it is contained. The carrier is obviously selected to minimize any degradation of the active ingredient and to minimize any adverse side effect in the subject, as is known for a person skilled in the art.

The effective dosages and administration timetables of the compositions comprising the activating or inhibitory compound described herein can be determined empirically, and making such determinations is within expertise in the art. The dosage intervals for the administration of the compositions are large enough to produce the desired anti-hypertrophic effect in the disorder. The dosage must not be so large that they cause adverse side effects, such as unwanted cross-reactions, anaphylactic reactions, and the like. Generally, the dosage varies with age, condition, sex and extent of the disease in the patient, the administration route, or if other drugs are included in the regimen, and can be determined by a person skilled in the art. The dosage can be adjusted by the individual physician in case of any contraindication. The dose may vary and can be administered in one or more daily dose administrations for one or several days. Guidelines can be found in the literature in relation to suitable dosages for given classes of pharmaceutical products.

The following example is provided to merely illustrate the present invention.

EXAMPLES

Example 1

Pitx2 and Muscle Regeneration

Based on the results shown in the drawings and taking into account that, interestingly enough, the expression of Pitx2 is significantly increased during muscle regeneration in mouse and decreased in the Duchenne muscular dystrophy murine model (DMDmdx mice), an experimental approach to an "in vivo" cell transplant was carried out to test if Pitx2 could improve the regenerative ability of isolated dystrophic muscle satellite cells. It is important to point out that the possibility of modifying the regenerative ability of actual dystrophic cells is a significant advantage for their therapeutic application in humans (possibility of using cells from a dystrophic patient). The obtained results allow clearly showing that the overexpression of Pitx2 improves the muscle regeneration carried out by dystrophic satellite cells by increasing muscle regeneration in MDX mice. Therefore, the results herein demonstrate that the transplant of dystrophic satellite cells overexpressing Pitx2 in DMDmdx mice leads to:

An increase in the number of myofibers formed "de novo" (FIG. 4A);

Repression of the expression of miR-31, producing restoration of dystrophin (FIG. 4B)

Finally producing a very significant functional improvement in muscle (FIG. 4C).

Therefore, these analyses led to identifying miR-31 as miRNA regulated by Pitx2 during muscle regeneration. Furthermore, additional evidence was also obtained that shows that the Pitx2-miRNAs pathway controlling cell proliferation is also present in "in vivo" the cell transplantation model used herein in DMDmdx mice (FIGS. 4D-F). Together, these results identify Pitx2 as a regulatory molecule of different miRNAs that play a fundamental role in molecular circuits controlling satellite cell proliferation and/or differentiation by showing the important role of Pitx2 in the cell biology of skeletal muscle satellite cells and identifying unknown functions of Pitx2 by modulating regenerative myogenesis in dystrophic muscle.

Example 2

Detailed Description of the Results of the Invention

Figure 2:
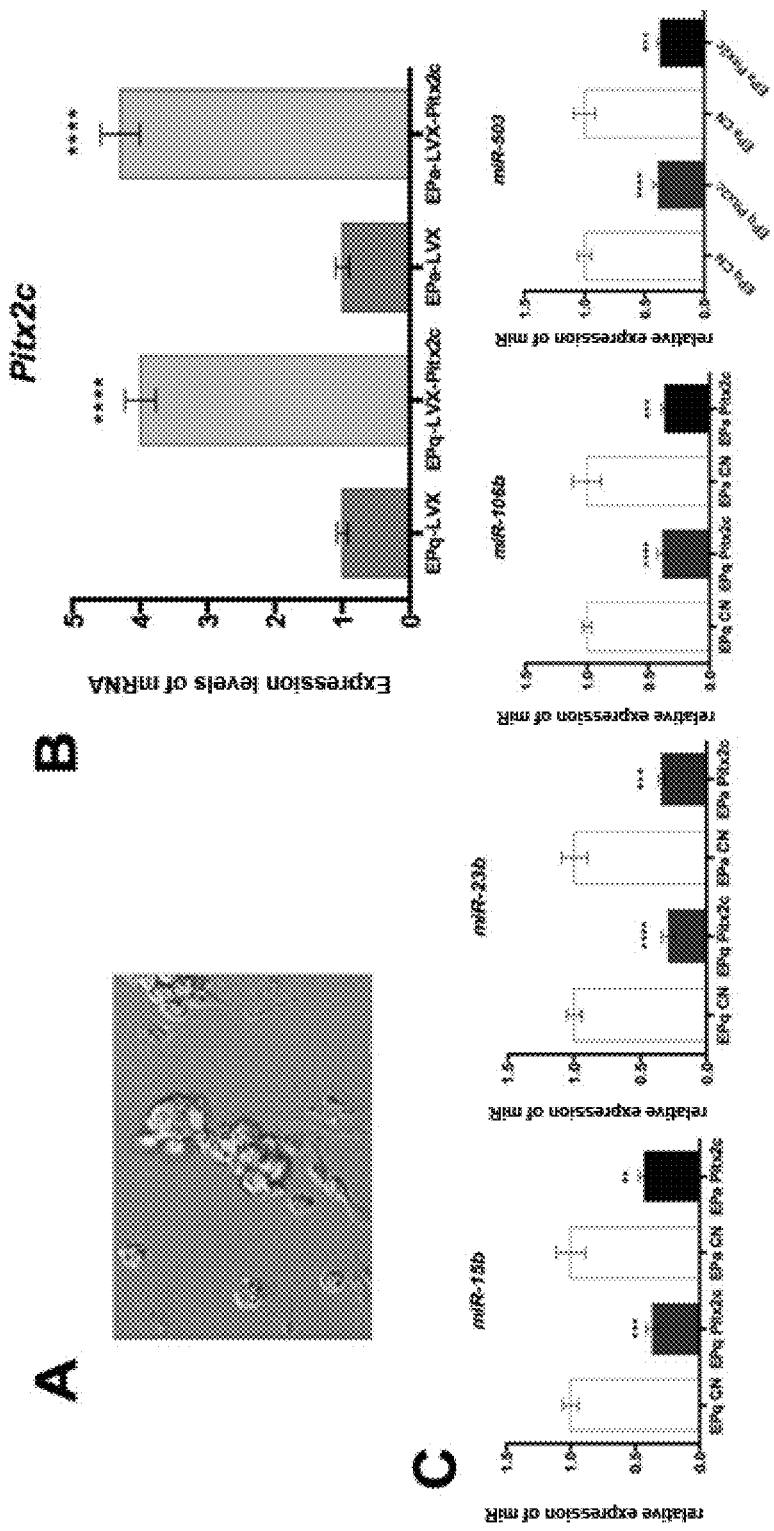
FIGS. 2. A and B) Overexpression of Pitx2 in mouse satellite cells by means of transfection with bicistronic lentiviral LVX-Pitx2c-ZSGreen vector. C) Expression of miRNAs: miR-15b, miR-106b, miR-23b and miR-503 (qRT-PCR) is reduced in satellite cells overexpressing Pitx2, in cells both in early stages of activation (EPq) and in more advanced stages of activation (EPa) (qRT-PCR). D) Transfection with bicistronic lentiviral LVX-Pitx2c-ZSGreen vector leads to a decrease in the expression of cell cycle control genes cyclin D1 and cyclin D2 (qRT-PCR), indicating that similarly to what occurs in myoblasts, the Pitx2-miRNAs pathway controls proliferation in satellite cells. E) Quantification by immunohistochemistry of the number of cells in proliferation (Ki67+) in cultures of satellite cells overexpressing Pitx2.
Figure 2:
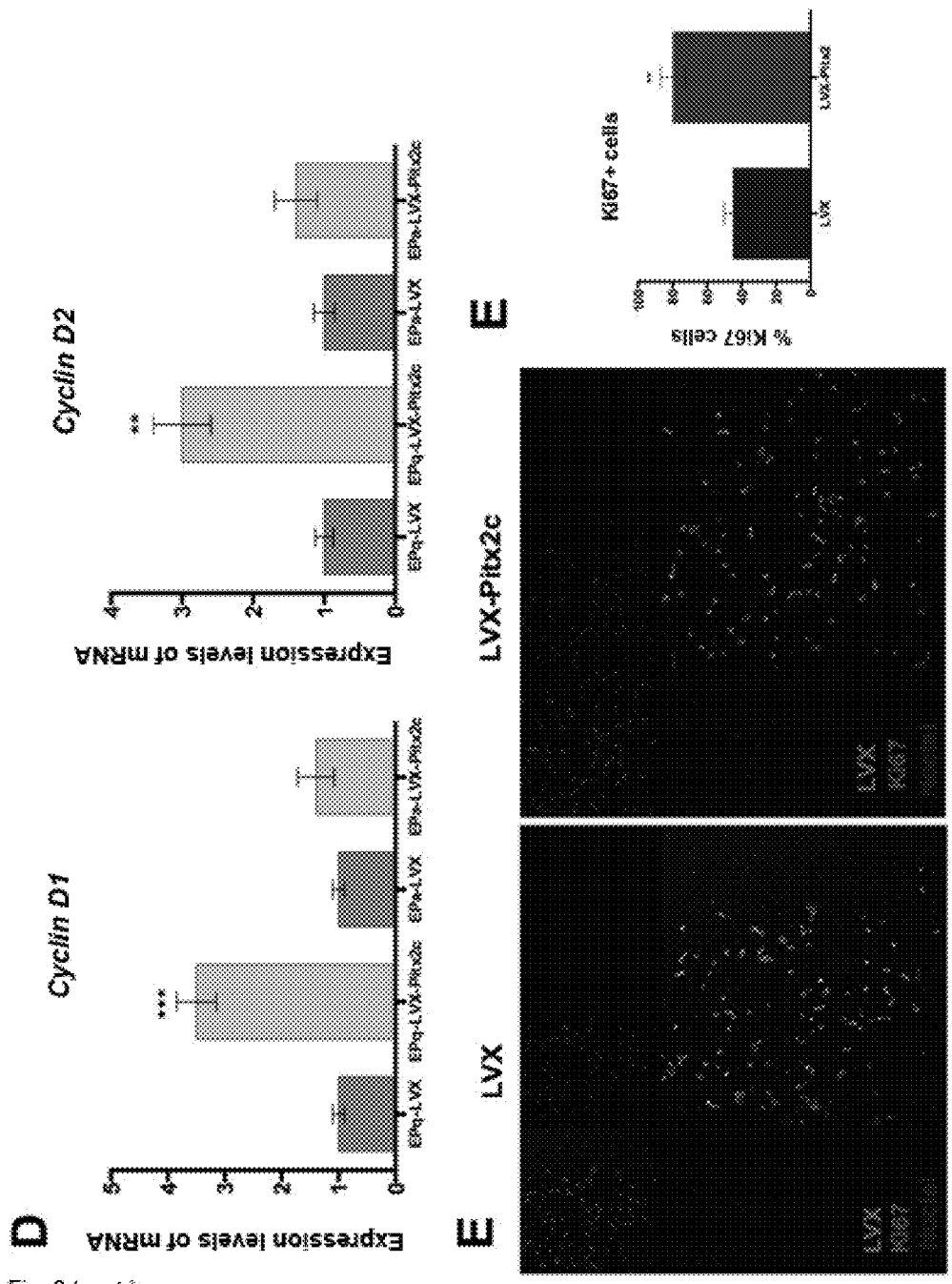

Firstly, as shown in FIGS. 2A) and B), transfection with bicistronic lentiviral LVX-Pitx2c-ZSGreen vector resulted in the overexpression of Pitx2 in mouse satellite cells. Additionally, this overexpression, see FIG. 2 C), resulted in a decreased expression of the miRNAs: miR-15b, miR-106b, miR-23b and miR-503 (qRT-PCR), in cells both in early stages of activation (EPq) and in more advanced stages of activation (EPa) (qRT-PCR).

In addition, as shown in FIG. 2D), transfection with bicistronic lentiviral LVX-Pitx2c-ZSGreen vector leads to a decrease in the expression of cell cycle control genes cyclin D1 and cyclin D2 (qRT-PCR), indicating that similarly to what occurs in myoblasts, the Pitx2-miRNAs pathway controls proliferation in satellite cells.

Secondly, as illustrated in FIG. 3 A), the expression of Myf5 (qRT-PCR) increases in satellite cells overexpressing Pitx2; furthermore, quantification by immunohistochemistry, see FIG. 3 B), shows a significant increase in Myf5+ cells. In addition, according to FIG. 3C), overexpression of miR-106b leads to a decrease in the expression of Myf5, validating it as a target of this miRNA. Moreover, normalized activity of the luciferase of Myf5 3'-UTR luciferase reporter (VVT Myf5 3'-UTR) with the empty plasmid (Vector) or co-transfecting with pre-miR-106b shows the loss of luciferase activity, indicating repression of the expression of Myf5 by miR-106b, therefore demonstrating that Myf5 is a direct target for miR-106b. There is no loss of luciferase activity when the miR-106b seed sequence was mutated, thereby demonstrating the binding specificity of miR-106b to these seed sequences of Myf5 3'UTR (see FIG. 3D))

Thirdly, as shown in FIG. 4A), analysis by means of qRT-PCR shows the overexpression of Pitx2c in MDX mouse muscles injected with dystrophic satellite cells transfected with lentiviral LVX-Pitx2c-ZS-Green vector compared to muscle injected with cells transfected with the empty lentivirus (LVX-ZS-Green vector); percentage of fibers formed "de novo" (ZS-Green+cells) in transplanted muscles after 15 days and representative image. In addition, FIG. 4B) shows how the decrease in the expression of miR-31 in muscles transplanted with cells overexpressing Pitx2 leads to an increase in expression levels of dystrophin and to a significant increase in fibers expressing dystrophin. Additionally, the authors of the present invention carried out a treadmill test, see FIG. 4C), which shows the functional improvement of DMDmdx mice injected with cells overexpressing Pitx2. Finally, FIG. 4F) shows how expression levels of cyclins D1 and D2 and of transcription factor Myf5 were increased in muscles transplanted with cells overexpressing Pitx2, indicating that the Pitx2-miRNA molecular cascade is conserved in the "in vivo" transplantation system.

Example 3

Figure 5:
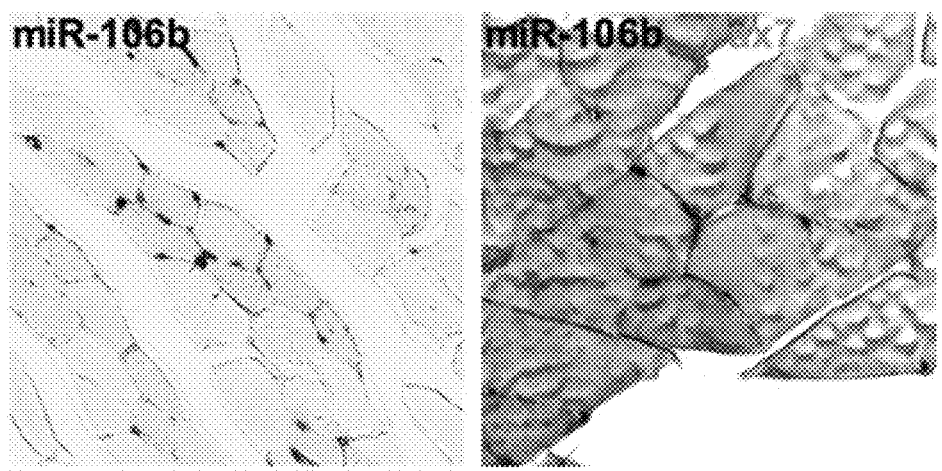
FIG. 5. LNA in situ for miR-106b. Joint expression with a specific marker for satellite cells (Pax7) (Lozano Velasco et al.; Mol Cell Biol, 2015)

Downrequlation in miR-106b In Vivo Mediated by Infection of the Anti-miR106b Compound Improves the Myogenic Regeneration Process in DMDmdx Mice The preceding examples show that miR-106b selects as a target Myf5 mRNA 3'UTR and that the downregulation in miR-106b in recently isolated satellite cells leads to the increase in the Myf5+ cell population. Furthermore, it has been detected by means of in situ LNA analysis that miR-106b carries out a tissue expression pattern compatible with the expression labeled in satellite cells (FIG. 5). These results showed a role for miR-106b boosting more optimal satellite cell populations for myogenic commitment and suggest that miR-106b plays an important role in regulating satellite cell activation and differentiation during muscle regeneration. Therefore, to further study these findings, the expression profile (the expression profile of miR-106b) during the muscle regeneration process in mice was first analyzed. The results clearly show that miR-106b is downregulated during the time interval comprised between days 3 and 7 after the injection of cardiotoxin (FIG. 6). Curiously, on day 3 from the injection of the antimiR-106b compound, a clear upregulation of Myf5, MyoD and myogenin was found, supporting the notion that se downregulation in miR-106b is required for suitable myogenic differentiation during the muscle regeneration process (FIG. 6).

Example 4

Downregulation in miR-106b In Vivo Mediated by Infection of the Anti-miR106b Compound Improves the Myogenic Regeneration Process in DMDmdx Mice To further study the role of miR-106b during muscle repair, it was investigated whether the expression of miR-106b changed in a context in which muscle regeneration is not completed satisfactorily, such as in DMD. In this sense, it was demonstrated that the expression of miR-106b clearly increases in MDX mouse muscles, an animal model that is widely used for human DMD (FIG. 7).

In summary, it was observed that the expression of miR-106b decreases during muscle regeneration but increases when muscle regeneration is not satisfactory. Therefore, it was then considered whether muscle regeneration in mice dystrophic could be modulated by decreasing the expression of miR-106b. To approach this issue, a strategy was developed by means of which cardiotoxin and miRNA inhibitor hsa-miR-106b-5p (ID: MH10067; Cat: 4464084, Ambion) (SEQ ID NO:3) were injected in TA muscle (tibialis anterior muscle) of 4 month old MDX mice (1.7 nmol per injection). After the injection of miRNA inhibitor, the muscles were removed 1, 3 and 15 days after the injection of anti-miR-106b compound for analysis. The results clearly show that the injection of anti-miR-106b compound can decrease the presence of miR-106b.

Interestingly enough, the decrease in miR-106b coincides with myogenic differentiation waves as observed by means of upregulation of Myf5, MyoD and myogenin, which indicates that decreased levels of miR-106b induced by means of injection of anti-miR106b compound can boost muscle differentiation (FIG. 8).

Figure 9:
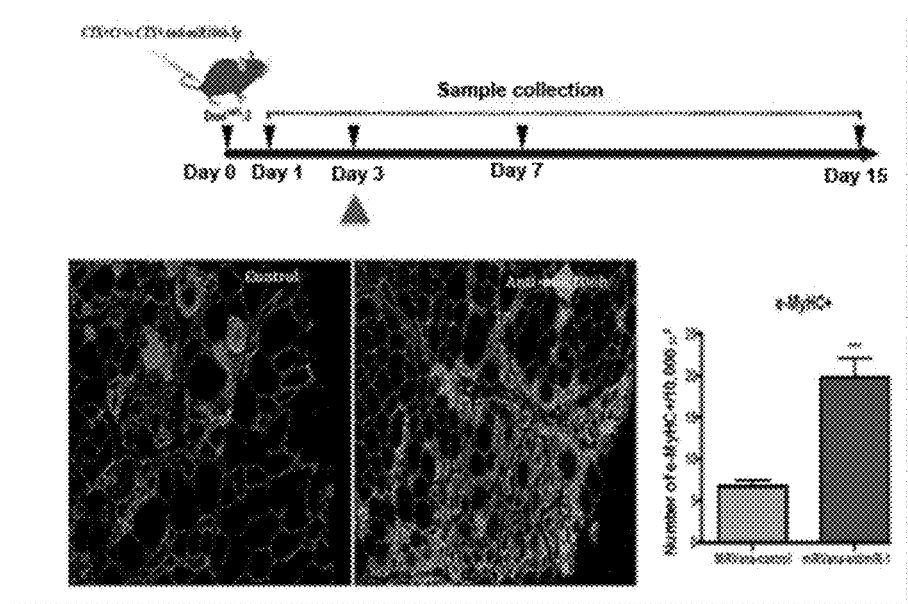
FIG. 9. Staining with e-MyHC antibody in muscles injected with anti-miR-106b compound and control 15 days after injection in the muscle and quantification of e-MyHC+ myofibers.
Figure 10:
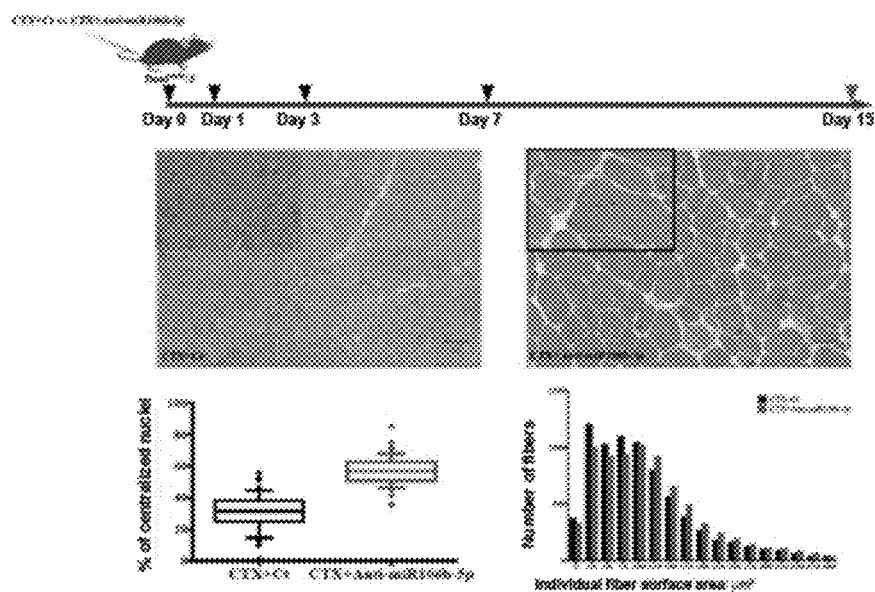
FIG. 10. Quantification of centralized nuclei and cross-section area in tibialis anterior (TA) muscles, muscles injected with anti-miR-106b compound compared with control muscles.

The new formation of myofibers was also analyzed using e-MyHC antibody, and it was found that the number of myofibers positive for e-MyHC was potentiated in muscles treated with anti-miR compound compared to the control, which demonstrates that recently formed myofibers increased after the injection of anti-miR-106b compound (FIG. 9). Furthermore, histological analyses of TA from DMDmdx/J mice 15 days after treatment with anti-miR-106b compound clearly show an increase in the percentage of fibers with centralized nuclei (FIG. 10). Furthermore, treatment with the anti-miR-106b compound induced a shift in the distribution of the size of fibers being regenerated towards classes having a larger surface area. Together, these results indicate that the regenerative potential was potentiated in DMD/mdx satellite cells after the injection of anti-miR-106b compound (FIG. 10).

Example 5

Evaluation of the Functional Yield

To evaluate the functional yield, treadmill tests to exhaustion were conducted in DMD/mdx mice injected with anti-miR106b compound 30 days after treatment with anti-miR-106b compound. As illustrated in FIG. 11, running time and distance were from 50% to 95% higher, respectively, in mice treated with anti-miR-106b compound with respect to the control, which indicates that the injection of anti-miR-106b compound strengthens physical performance.

When considered together, the results showed that miR-106b plays a key role during the muscle regeneration process in mice. Furthermore, the data herein presented demonstrated that the intramuscular injection of anti-miR-106b compound can improve the ability of regeneration in DMD mice.

The invention claimed is:

1. A method of promoting muscle regeneration in a human or animal subject, the method comprising administering to the subject an effective amount of a composition comprising a compound that is capable of reducing the expression of miRNA-106b in muscle satellite stem cells.

2. The method according to claim 1, wherein said compound is selected from the group consisting of:
   a. an interfering RNA (siRNA) of miRNA-106b;
   b. an antisense RNA oligonucleotide of miRNA-106b;
   c. the miRNA inhibitor hsa-miR-106b-5p ID: MH10067, Cat: 4464084 (SEQ ID NO:3); and
   d. a polynucleotide comprising or consisting of a nucleotide sequence identical by at least 90% to the nucleotide sequence of the hsa-miR-106b-5p ID: MH10067; Cat: 4464084 (SEQ ID NO:3), wherein the polynucleotide is capable of inhibiting miR-106b.

3. The method according to claim 2, wherein said compound is selected from (c) or (d).

4. The method according to claim 1, wherein said compound is comprised in a vector or plasmid capable of transporting or delivering said compound to muscle satellite stem cells.

5. The method according to claim 4, wherein said vector is a viral vector.

6. The method according to claim 5, wherein said viral vector is selected from:
   (a) an adenoviral vector;
   (b) a lentiviral vector;
   (c) a retroviral vector; and
   (d) an adeno-associated vector.

7. The method according to claim 1, wherein said compound comprises a muscle satellite stem cell of a human or animal subject that was treated, transformed, transfected or transduced with:
   (a) an interfering RNA (siRNA) of miRNA-106b;
   (b) an antisense RNA oligonucleotide of miRNA-106b;
   (c) the miRNA inhibitor hsa-miR-106b-5p ID: MH10067, Cat.: 4464084 (SEQ ID NO:3); or
   (d) a polynucleotide comprising or consisting of a nucleotide sequence identical by at least 90% to the nucleotide sequence of the hsa-miR-106b-5p ID: MH10067; Cat: 4464084 (SEQ ID NO:3), wherein the polynucleotide is capable of inhibiting miR-106b.

8. The method according to claim 1, wherein said subject has a dystrophinopathy.

9. The method according to claim 8, wherein said dystrophinopathy is selected from Duchenne muscular dystrophy and Becker muscular dystrophy.

10. The method according to claim 1, wherein said subject is a human subject and wherein said composition is administered intramuscularly.

11. The method according to claim 10, wherein said composition is administered intramuscularly in a lower limb of said human subject.

12. The method according to claim 3, wherein said subject is a human subject and wherein said composition is administered intramuscularly in a lower limb of said human subject.

13. The method according to claim 10, wherein said human subject suffers from a dystrophinopathy.

14. The method according to claim 13, wherein said dystrophinopathy is selected from Duchenne muscular dystrophy and Becker muscular dystrophy.

15. The method according to claim 7, wherein said muscle satellite stem cell was treated, transformed, transfected or transduced with a vector or a plasmid comprising any one of (a)-(d).

16. The method of claim 15, wherein said muscle satellite stem cell was treated, transformed, transfected or transduced with a viral vector comprising any one of (a)-(d).

17. The method of claim 16, wherein said viral vector is selected from an adenoviral vector, a lentiviral vector, a retroviral vector, or an adeno-associated vector.

* * * * *